United States Patent [19]

Donlevy et al.

[11] Patent Number: 4,612,160
[45] Date of Patent: Sep. 16, 1986

[54] POROUS METAL COATING PROCESS AND MOLD THEREFOR

[75] Inventors: Alfred L. Donlevy; Clifford M. Bugle, both of Pittsburgh, Pa.

[73] Assignee: Dynamet, Inc., Washington, Pa.

[21] Appl. No.: 595,920

[22] Filed: Apr. 2, 1984

[51] Int. Cl.$^4$ .......................... B22F 3/10; B22F 7/08; A61F 2/34; A61L 27/00

[52] U.S. Cl. ..................... 419/2; 128/92 C; 419/9; 419/54

[58] Field of Search .............. 419/2, 54, 9; 128/92 C

[56] References Cited

U.S. PATENT DOCUMENTS

| | | | |
|---|---|---|---|
| 2,946,681 | 7/1960 | Probst et al. | 419/2 |
| 3,066,391 | 12/1962 | Vordahl | 29/182.5 |
| 3,181,947 | 5/1965 | Vordahl | 75/206 |
| 3,295,346 | 1/1967 | Bomberger, Jr. | 72/41 |
| 3,341,325 | 9/1967 | Cloran | 75/225 |
| 3,450,528 | 6/1969 | Thompson | 75/203 |
| 3,605,123 | 9/1971 | Hahn | 3/1 |
| 3,808,606 | 5/1974 | Tronzo | 3/1 |
| 3,840,904 | 10/1974 | Tronzo | 3/1 |
| 3,852,045 | 12/1974 | Wheeler et al. | 419/2 |
| 3,855,638 | 12/1974 | Pilliar | 3/1 |
| 3,905,777 | 9/1975 | Lacroix | 29/183.5 |
| 3,973,277 | 8/1976 | Semple et al. | 3/1 |
| 4,017,911 | 4/1977 | Kafesjian et al. | 3/1.5 |
| 4,156,943 | 6/1979 | Collier | 419/2 |
| 4,206,516 | 6/1980 | Pilliar | 3/1.9 |
| 4,261,063 | 4/1981 | Blanquaert | 3/1.91 |
| 4,351,069 | 9/1982 | Ballintyn et al. | 3/1.912 |
| 4,365,356 | 12/1982 | Broemer et al. | 3/1.9 |

Primary Examiner—Allan M. Lieberman
Attorney, Agent, or Firm—Webb, Burden, Robinson & Webb

[57] ABSTRACT

A process and mold for applying a porous metal coating to a metal substrate or a portion thereof, especially for forming a medical prosthesis. The substrate to be coated is cleaned, then positioned in a rigid mold of ceramic or metal material having a defined mold cavity. The space between the mold cavity surface and the substrate is filled with a metal powder and the mold, powder and substrate assembly is pre-sintered. The pre-sinter conditions are selected such that the powder lightly sinters together and adheres to the substrate, but not to the mold cavity surface. After removal of the mold, the coated substrate is further sintered to obtain the proper desired bond strength and pore volume. Sintering is carried out in a protective atmosphere.

21 Claims, 6 Drawing Figures

POROUS METAL COATING PROCESS AND MOLD THEREFOR

BACKGROUND OF THE INVENTION

1. Field of the Invention

This invention relates to a process for applying a porous metal coating to a metal substrate or a portion thereof and more particularly, a porous coating of a reactive metal such as titanium or titanium base alloy applied to a substrate of similar base material. The invention also relates to a mold for use in the process. The process and mold are especially, although not exclusively, useful for making medical prostheses.

2. Brief Description of the Prior Art

Prior art descriptions and practices applicable to titanium and other reactive metals utilize either flame spraying or adhesive bonding, followed by high temperature sintering, to produce a porous coating on a metal substrate. While these former processes are useful to produce porous coated products, the products are subject to substantial dimensional variation. Moreover, the thickness of the porous coating is also subject to considerable variation due to application techniques. Furthermore, with reactive metal systems, contamination of the applied coating by the adhesive is a definite problem.

The desirability of producing porous surfaces on medical prosthetic devices is well documented, for example in Pilliar U.S. Pat. No. 3,855,638. Hahn U.S. Pat. No. 3,605,123 and Kafesjian et al. U.S. Pat. No. 4,017,911 describe methods of producing such porous coatings. Further, Tronzo U.S. Pat. No. 3,808,606 also describes medical devices having porous surfaces.

The various medical factors involved in bone or tissue ingrowth or even those involved in bone cement adhesion are well-known to those in the art and need not be discussed in detail herein. However, the medical community has clearly indicated that control of the pore size in porous coatings is highly desirable and dimensional control absolutely necessary for satisfactory prosthetic devices. Additionally, careful control of chemistry and the elimination of sources of contamination are also recognized to be essential for implanted prosthetic devices.

The known flame spray method as illustrated by Hahn Pat. No. 3,605,123 of applying a coating to a metal substrate has two major limitations. The control of pore size and volume is difficult due to the very nature of this method and the control of the dimensional characteristics of the coating is also complex.

The use of adhesives as described in U.S. Pat. Nos. 3,808,606 and 4,017,911 overcomes the porosity problems associated with the flame spray method; however, products made with adhesives also are subject to considerable dimensional variation. As important, the use of glue or other adhesives on reactive metals such as titanium frequently involves contamination of the pore-producing media, i.e. powder, as well as contamination of the substrate itself.

Tronzo U.S. Pat. No. 3,840,904 discloses an acetabular hip prosthesis and suggests the desirability of anchoring a prosthesis using a porous coating. However, the patent does not disclose any method or apparatus for applying the coating to a substrate or to a portion thereof.

SUMMARY OF THE INVENTION

The present invention enables the production of porous coated parts to close tolerances, without contamination of the coating materials or the substrate. This is accomplished preferably by the utilization of a reusable ceramic or metal form or mold. The mold is manufactured to close tolerances with provisions made to accurately position the substrate or that portion of the substrate to be porous coated. The mold is constructed to have the shape and contour of the final part, allowing for any shrinkage that is anticipated during sintering.

According to the process of the invention, the substrate or substrate portion to be coated is cleaned and positioned within the mold cavity. The space between the mold cavity and substrate is filled with powder and the assembly consisting of the mold, powder and substrate is pre-sintered at a relatively low temperature. The pre-sinter conditions are carefully controlled such that the powder lightly sinters together and adheres to the substrate but not to the mold cavity. After removal of the mold form, the pre-sintered substrate and powder coating are further sintered at a higher temperature to obtain the proper and desired bond strength and pore volume.

Briefly, the invention is a process for producing a porous metal coating on at least a portion of a metal substrate utilizing a rigid mold comprising the steps of: providing a mold having a cavity of such a size as to receive therein that portion of the metal substrate to be coated with a space between the mold cavity and a surface of the substrate portion to be coated; disposing the substrate portion to be coated in the mold cavity; disposing metal powder in the space between the mold cavity and the surface to form an assembly of the mold, the metal powder and the substrate portion; pre-sintering the assembly to cause the metal powder to adhere to the substrate portion, but not to the mold cavity; removing the coated substrate portion from the mold; and further sintering the coated substrate portion, the sintering steps being carried out in a protective atmosphere.

The invention also includes a metal or ceramic mold for performing the process.

The present method provides an intimate bond of a layer of particulate material to metal substrate. The method is especially suitable for applying a porous coating to a reactive metal where closely toleranced coated parts are required. By utilizing proper mold design, the porous coating may be applied to an entire substrate or only to selected portions of the substrate.

The invention will be better understood and additional techniques and advantages will become apparent to those skilled in the art from the following detailed description of the preferred embodiments of the invention when taken with the accompanying drawings. Various changes in the details and methods of the invention will also be apparent to those skilled in the art. Such modifications are within the scope of the invention which is especially useful for, but is not limited to, the production of medical devices such as prostheses.

BRIEF DESCRIPTION OF THE DRAWINGS

In the accompanying drawings illustrating the invention.

DESCRIPTION OF THE PRESENTLY PREFERRED EMBODIMENTS OF THE INVENTION

Figure 1:
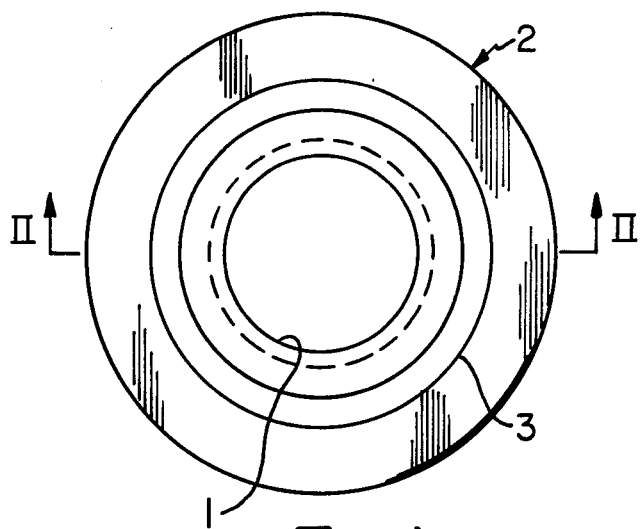
FIG. 1 is a top plan view of a mold for porous coating a portion of a metal substrate in the form of an acetabular hip cup according to the invention.

Three examples of the invention are described hereinafter. Example I involves the utilization of a ceramic mold to make a porous coated substrate in the form of an acetabular hip cup having a uniform shape. Example II describes a metal mold to make a porous coated hip cup having a uniform shape and including provision for bone screws. Example III describes the use of a mold to make a complex or geometrically non-uniform porous coated shape in the form of a hip prosthesis. The same reference numerals refer to like elements. The mold may be reusable or disposable.

EXAMPLE I

Figure 2:
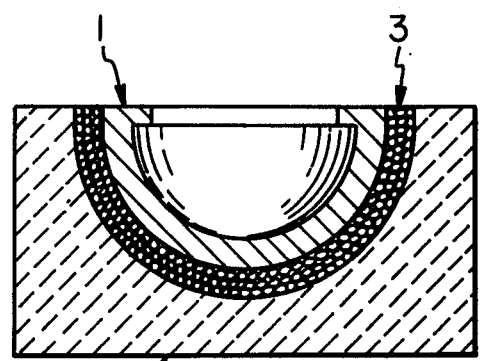
FIG. 2 is a cross-sectional view taken along the lines II—II of FIG. 1.

FIGS. 1 and 2 show a mold for porous coating a substrate in the form of an acetabular hip cup. A substrate 1 was prepared from commercially pure titanium by conventional forming and machining techniques. The outer surface of the substrate was in the form of a hemisphere of 48 mm diameter which has a tolerance of plus or minus 0.1 mm.

A cylindrical mold 2 was prepared from a refractory oxide, namely 99% alumina ceramic. The hemisphere in the mold had a diameter of 50 mm. The manufacturing tolerance on the 50 mm dimension was plus or minus 0.05 mm.

Commercially pure titanium powder 3 in the form of small spheres or particles was positioned in the space in the mold cavity between substrate 1 and the mold 2. The spherical powder is made preferably in an inert chamber by a process called the Rotating Electrode Process. This powder is commercially available from Nuclear Metals Inc., Concord, Mass.; however, other suitable powders may be used.

The powder was screened to obtain a powder size between 40 and 60 mesh, U.S. Standard Sieve. By controlling the powder size, the pore size is indirectly controlled.

The technique for positioning the powder comprised weighing the proper quantity of powder, placing the powder in the mold 2 and then settling the substrate 1 down into the mold cavity, with modest vibration by hand or mechanical means. The powder flowed up the spherical surface of the mold cavity and substantially uniformly filled the space between the substrate 1 and the mold 2. The vibration also insured nearly ideal packing of the powder spheres or particles.

The entire assembly consisting of the substrate 1, powder 3 and mold 2 was placed into a conventional muffle furnace having a protective atmosphere. The furnace was then evacuated and the assembly was heated to the proper temperature to pre-sinter the coating to the substrate. The pre-sintering temperature utilized in this example was 1900° F. for two hours. However, satisfactory results have been obtained using a pre-sintering temperature of 1550° F. for −100 mesh powder and 2100° F. for −30 +40 mesh powder.

After pre-sintering was complete, the mold 1 was removed. The accurately formed powder coating adhered to the substrate. The coated substrate was then transferred to a high temperature furnace for final sintering. The product was sintered at 2400° F. for four hours. Again, the appropriate temperature for final sintering is dependent upon the powder size, the furnace atmosphere, and the pore volume and interface strength desired.

Upon completion of the process, the pore volume of the porous coating was approximately 40% and the shear strength of the powder-substrate interface exceeded 2000 psi. The size of the finished coated product was 49.90 mm and the spherical radius was true within plus or minus 0.07 mm.

EXAMPLE II

Figure 3:
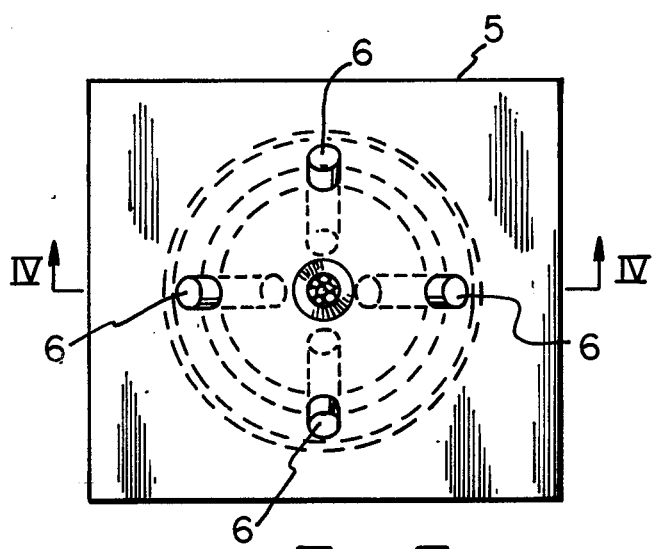
FIG. 3 is a top plan view of a second embodiment of a mold for porous coating a portion of a metal substrate in the form of an acetabular cup having holes in the cup for bone screws.
Figure 4:
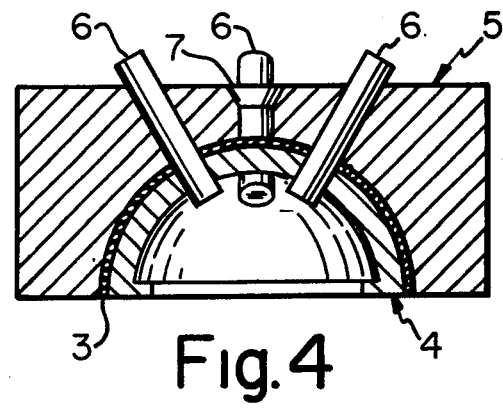
FIG. 4 is a cross-sectional view taken along the lines IV—IV of FIG. 3.

A second example of the invention will be described in connection with FIGS. 3 and 4. A titanium alloy part 4 made from Ti-6Al-4V ELI (Extra Low Interstitial) alloy is positioned within rectangular mold 5. The mold is machined from molybdenum metal. Dowels or pegs 6 made from an alumina ceramic are provided to produce circular holes through the porous coating in alignment with holes in the machined part 4.

Titanium alloy powder, specifically Ti-6Al-4V alloy, of −60 +80 mesh is introduced through the fill port 7. The assembly is vibrated to flow the powder down around the part, where it fills the space uniformly with nearly theoretical packing of the spheres. The assembly is then pre-sintered at 1850° F. in vacuum for one hour.

After the pre-sinter, the ceramic pegs 6 are first removed and then the molybdenum mold 5 is stripped from the coated part. The part is then finally sintered at 2300° F. for eight hours in vacuum.

Test coupons of the same substrate having the same powder distribution and subjected to the same sintering conditions as the completed product included 30% voids and the alloy powder tightly adhered thereto, illustrating that the resulting product would achieve the same results with excellent detail around the holes formed by the ceramic pegs.

EXAMPLE III

Figure 5:
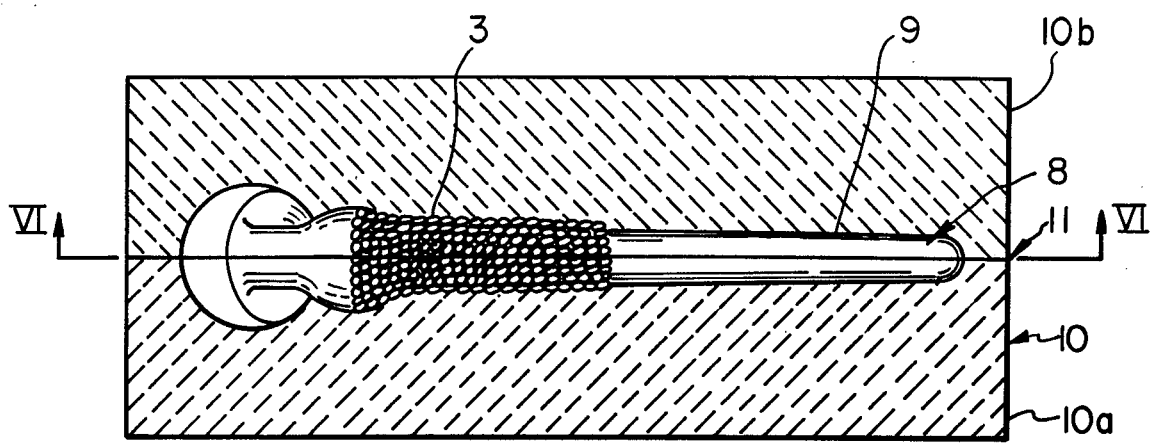
FIG. 5 is a cross-sectional view taken along the lines V—V of FIG. 6 but showing a complete complex non-uniform hip prosthetic device with a partly porous coated stem in the mold.
Figure 6:
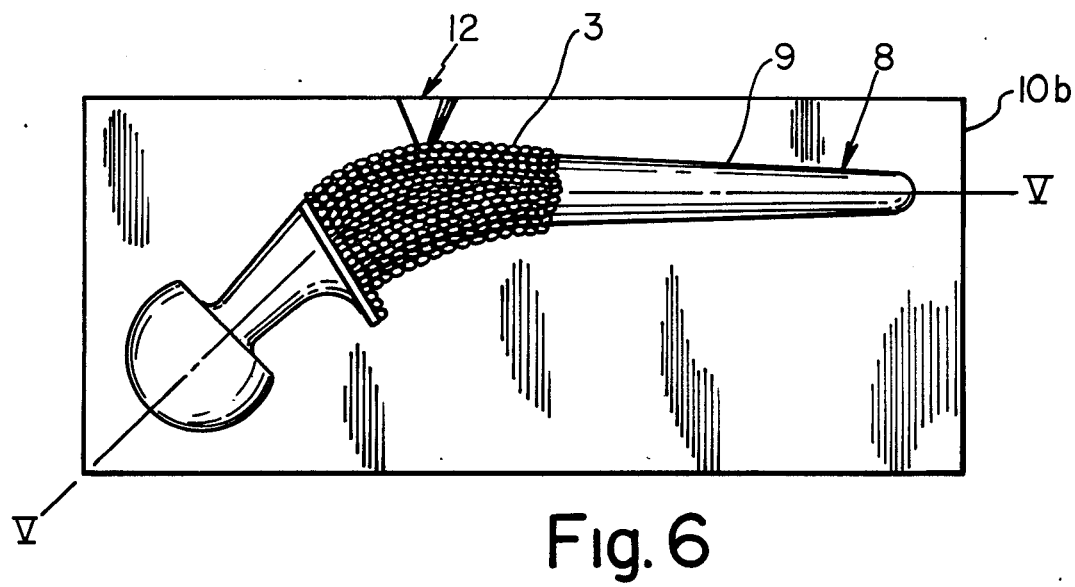
FIG. 6 is a cross-sectional view taken along the lines VI—VI of FIG. 5, also showing the complete prosthetic device positioned in the mold.

The utility of the invention is not limited to geometrically uniform shapes of the type described in the previous examples. More complex shapes will be described in connection with FIGS. 5 and 6. In this example, it is desired to make a hip prosthesis part 8 to be coated in specific areas on the stem 9 of the prosthesis where the device could be in contact with the femur when surgically implanted in a human.

The ceramic mold 10 is split into two mold sections 10a and 10b along its longitudinal axis 11 to permit removal of the part 8 after the pre-sinter operation. In this example Ti-6Al-4V ELI alloy is utilized.

The spherical powder of Ti-6Al-4V alloy is introduced into the space between the part and the mold as described in the previous example through the fill port 12. The particle size of the powder is −30 +40 mesh.

Pre-sintering is performed at 2000° F. for one hour in flowing argon.

After removal of the mold sections 10a, 10b, the porous coated part 8 is then sintered at 2500° F. for six hours. Again, based upon test coupon results, a uniform accurately defined coating is produced with 40% void fraction and over 2000 psi shear strength of the coating to the base part interface.

Preferably, the ceramic molds used in the invention are constructed from materials classified as oxide ceramics. Alumina ($Al_2O_3$) and stabilized zirconia ($ZrO_2+CaO$) are most useful due to their chemical inertness, availability, and relative economy. However, those skilled in the art will recognize that thoria ($ThO_2$), beryllia (BeO), spinel ($MgAl_2O_4$) and other oxide ceramic systems are also suitable materials for the practice of the invention. Further, ceramic nitrides such as boron nitride are useful in mold construction.

Molds made of high temperature materials, such as nickel and cobalt base alloys, and refractory metals may be used.

In this connection, boron nitride or yttria may be applied by painting, dusting or the like to the cavity of a metal mold before the substrate and powder are disposed therein. The material acts as a release agent to facilitate separation of the porous coating from the mold cavity after pre-sintering.

Sintering is carried out in a protective atmosphere. The atmosphere used in Example I was vacuum, but it may be an inert gas. Hydrogen has been utilized, but the use of hydrogen with titanium involves the undesirable risk of forming excessive titanium hydride under certain cooling conditions. Argon is the preferred atmosphere for the pre-sintering step; however, other inert gases may be used.

As the Examples demonstrate, the proper temperature is determined by the shape of the product to be produced, the total thickness of the powder coating desired, and the particle size of the powder. In selecting the proper temperature the reactivity of the mold must also be considered, as well as the handling requirements of the presintered product prior to final sintering.

As a general rule, it may be said that the larger the particle size of the metal powder to be coated, the higher the temperature; the smaller the size of the metal powder particles, the lower the temperature used. Moreover, appropriate adjustments may be made, as is well recognized by those skilled in the art, to either the sintering time or the temperature or both in order to achieve the desired product.

Having described presently preferred embodiments of the invention, it is understood that it may otherwise be embodied within the scope of the appended claims.

We claim:

1. A process for producing a porous metal coating on at least a portion of a reactive metal substrate utilizing a rigid mold comprising the steps of:
    (a) providing a mold having a cavity of such a size as to receive therein that portion of the metal substrate to be coated with a space between the mold cavity and a surface of the substrate portion to be coated;
    (b) disposing the substrate portion to be coated in the mold cavity;
    (c) disposing reactive metal powder in the space between the mold cavity and the surface to form an assembly of the mold, the metal powder and the substrate portion;
    (d) pre-sintering the assembly to cause the metal powder to adhere to the substrate portion, but not to the mold cavity;
    (e) removing the coated substrate portion from the mold; and
    (f) further sintering the coated substrate portion, the sintering steps being carried out in a non-reactive atmosphere.

2. The process as set forth in claim 1 wherein the non-reactive atmosphere is vacuum.

3. The process as set forth in claim 1 wherein at least one of the metal powder and the substrate is selected from the group consisting of titanium and titanium base alloys.

4. The process as set forth in claim 1 wherein the mold is made of ceramic material.

5. The process as set forth in claim 4 wherein the ceramic material is selected from the group consisting essentially of alumina, zirconia and yttria.

6. The process as set forth in claim 1 wherein the mold is made of a high temperature material selected from the group consisting of nickel and cobalt base alloys.

7. The process as set forth in claim 1 wherein the mold is made of a refractory metal.

8. The process as set forth in claim 1 wherein a ceramic release agent is applied to the mold cavity prior to disposition therein of the substrate portion to be coated.

9. The process as set forth in claim 1 wherein the pre-sintering atmosphere is argon and the final sintering atmosphere is vacuum.

10. The process as set forth in claim 1 wherein at pre-sintering and final sintering temperatures the pre-sintering and final sintering atmosphere is hydrogen.

11. The process as set forth in claim 1 wherein the metal powder has a particle size of about $-20$ and $+200$ mesh.

12. The process as set forth in claim 1 wherein the metal powder has a particle size of about $-35$ and $+80$ mesh.

13. The process as set forth in claim 1 wherein the pre-sintering temperature is between about 1550° F. and about 2100° F.

14. The process as set forth in claim 13 wherein the pre-sintering is carried out for about 2 hours.

15. The process as set forth in claim 1 wherein the final sintering is carried out between about 2000° F. and about 2500° F.

16. The process as set forth in claim 15 wherein the final sintering is carried out for about 4 hours.

17. The process as set forth in claim 1 wherein the powder has a particle size of between about $-40$ and $+60$ mesh, the pre-sintering step is carried out at about 1900° F. for 2 hours and the final pre-sintering is carried out at about 2400° F. for about 4 hours.

18. The process as set forth in claim 1 wherein the powder has a particle size of about $-60$ and $+80$ mesh, the pre-sintering temperature is about 1850° F. for about 1 hour, and the final sintering temperature is about 2300° F. for about 8 hours.

19. The process as set forth in claim 1 wherein the powder has a particle size of about $-30$ and $+40$ mesh, the pre-sintering temperature is about 2000° F. to about 1 hour, and the final sintering temperature is about 2500° F. for about 6 hours.

20. The process as set forth in claim 1 wherein the shape of the substrate is geometrically non-uniform.

21. The process as set forth in claim 1 wherein the metal powder and the substrate are selected from the group consisting of titanium and titanium alloys.

* * * * *